(12) United States Patent
DiSilvestro et al.

(10) Patent No.: US 7,896,869 B2
(45) Date of Patent: Mar. 1, 2011

(54) SYSTEM AND METHOD FOR ENSURING PROPER MEDICAL INSTRUMENT USE IN AN OPERATING ROOM

(75) Inventors: Mark R. DiSilvestro, Columbia City, IN (US); Terry Dietz, Columbia City, IN (US); Jason T. Sherman, Warsaw, IN (US); Robert Hastings, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 911 days.

(21) Appl. No.: 11/049,805

(22) Filed: Feb. 3, 2005

(65) Prior Publication Data

US 2006/0142739 A1 Jun. 29, 2006

Related U.S. Application Data

(60) Provisional application No. 60/640,155, filed on Dec. 29, 2004.

(51) Int. Cl.
*A61B 17/00* (2006.01)
*G06F 19/00* (2006.01)

(52) U.S. Cl. .............................. 606/1; 128/898; 700/245

(58) Field of Classification Search .................... 600/1; 128/897–898; 606/34, 37; 434/262; 700/245–249, 700/258–264; 901/1, 2, 9
See application file for complete search history.

(56) References Cited

U.S. PATENT DOCUMENTS

| | | | |
|---|---|---|---|
| 4,974,166 A | 11/1990 | Maney et al. | |
| 5,443,082 A | 8/1995 | Mewburn et al. | |
| 5,572,999 A | 11/1996 | Funda et al. | |
| 6,158,437 A * | 12/2000 | Vagley | 128/898 |
| 6,285,902 B1 | 9/2001 | Kienzle, III et al. | |
| 6,591,239 B1 | 7/2003 | McCall et al. | |
| 6,847,336 B1 | 1/2005 | Lemelson et al. | |
| 7,164,968 B2 * | 1/2007 | Treat et al. | 700/245 |
| 2002/0143320 A1 | 10/2002 | Levin | |
| 2003/0069644 A1 | 4/2003 | Kovacevic et al. | |
| 2003/0093503 A1 | 5/2003 | Yamaki et al. | |
| 2003/0216836 A1 * | 11/2003 | Treat et al. | 700/245 |
| 2004/0044295 A1 * | 3/2004 | Reinert et al. | 600/587 |
| 2004/0073279 A1 | 4/2004 | Malackowski | |
| 2004/0078219 A1 | 4/2004 | Kaylor et al. | |

FOREIGN PATENT DOCUMENTS

| | | |
|---|---|---|
| WO | WO 95/27252 A1 | 10/1995 |
| WO | WO 00/47103 | 8/2000 |
| WO | WO 2004/028627 | 4/2004 |
| WO | WO 2004/030757 | 4/2004 |
| WO | WO 2004/030759 | 4/2004 |

OTHER PUBLICATIONS http://www.roboticsurgicaltech.com/info/infoSafety.htm, Robotic Surgical Tech, Inc., "Safety", Printed from website on Jun. 29, 2005, 2 pgs. http://www.roboticsurgicaltech.com/info/infoServer.htm, Robotic Surgical Tech, Inc., "Instrument Prediction", Printed from website on Jun. 29, 2005, 2 pgs.
http://www.roboticsurgicaltech.com/info/infoPenelope.htm, Robotic Surgical Tech, Inc., "Using Penelope", Printed from website on Jun. 29, 2005, 3 pgs.
European Search Report for European Application No. EP05257907.5-2318 , Apr. 27, 2006, 3 pgs.

* cited by examiner

*Primary Examiner* — Michael Peffley
(74) *Attorney, Agent, or Firm* — Barnes & Thornburg LLP

(57) ABSTRACT

A system for managing medical instrument use during a surgical procedure may comprise a number of medical instruments, a display device configured to display any of the number of medical instruments, a microphone for transmitting voice commands identifying different ones of the number of medical instruments, and a controller. The controller is responsive to the voice commands to control the display device to display corresponding ones of the number of medical instruments.

29 Claims, 6 Drawing Sheets

SYSTEM AND METHOD FOR ENSURING PROPER MEDICAL INSTRUMENT USE IN AN OPERATING ROOM

CROSS-REFERENCE TO RELATED U.S. PATENT APPLICATION

This patent application claims priority to and the benefit of U.S. Provisional Patent Application Ser. No. 60/640,155, filed Dec. 29, 2004, the disclosure of which is incorporated herein by reference.

FIELD OF THE INVENTION

The present invention relates generally to systems for enhancing surgical techniques and processes, and more specifically to such systems for ensuring that medical instruments are used during surgical procedures according to a specified medical device usage sequence.

BACKGROUND

During the lifetime of a patient, it may be desirable to perform one or more surgical procedures on the patient as a result of, for example, disease or trauma. A number of medical instruments may be utilized during the performance of such a procedure.

SUMMARY

The present invention may comprise one or more of the features recited in the attached claims, and/or one or more of the following features and combinations thereof. A system for managing medical instrument use during a predefined surgical procedure may include a number of medical instruments. A display device may be configured to display any of the number of medical instruments. A controller may be configured to control the display device to sequentially display specified ones of the number of medical instruments to be used during a surgical procedure. The specified ones of the number of medical instruments may be sequentially displayed in an order defined by the surgical procedure.

The display device may be a monitor coupled to the controller. The monitor may include a display screen configured to display any of the medical instruments.

The system may further include a feedback device actuatable to provide information back to the controller. The feedback device may be actuatable to prompt the controller to control the display device to display a first one of the number of medical instruments to be used during the surgical procedure. The feedback device may further be actuatable to notify the controller when the first one of the number of medical instruments to be used during the surgical procedure has been selected for use. The controller may be responsive to the notice that the first one of the number of medical instruments to be used during the surgical procedure has been selected for use to control the display device to display the notice. The feedback device may be actuatable to notify the controller when use of the first one of the number of medical instruments to be used during the surgical procedure is complete. The controller may be responsive to the notice that the use of the first one of the number of medical instruments to be used during the surgical procedure is complete to control the display device to display the next one of the number of medical instruments in the order defined by the surgical procedure.

At least two of the number of medical instruments may cooperate to form a single instrument. The controller may be configured to control the display device to simultaneously display the at least two of the number of medical instruments to thereby display the single instrument.

The system may be operated in tandem with a computer assisted surgery system.

A method of managing medical instrument use during a predefined surgical procedure may comprise a number of steps. For example, the method may include the step of displaying a first one of a number of medical instruments to be used in the predefined surgical procedure. Another step may be displaying a next one of the number of medical instruments to be used in the predefined surgical procedure when use of the previous one of the number of medical instruments is complete. A further step may be repeating the step of displaying the next one of the number of medical instruments until all of the number of medical instruments to be used in the predefined surgical procedure have been used.

The step of displaying the next one of the number of medical instruments may include providing a signal when the use of the previous one of the number of medical instruments is complete. The step of displaying the next one of the number of medical instruments may include displaying the next one of the number of medical instruments to be used in the predefined surgical procedure only after the signal is received indicating that use of the previous one of the number of medical instruments is complete.

The step of displaying a first one of a number of medical instruments to be used in the predefined surgical procedure may include displaying the first one of the number of medical instruments on a video monitor. Alternatively or additionally, the step of displaying a first one of a number of medical instruments to be used in the predefined surgical procedure may include displaying at least a subset of the number of medical instruments including the first one of the number of medical instruments on a video monitor. The step of displaying a first one of a number of medical instruments to be used in the predefined surgical procedure may include displaying at least a subset of the number of medical instruments including the first one of the number of medical instruments via a video projector onto a surface.

A system for managing medical instrument use during a surgical procedure may comprise a number of medical instruments. A display device may be configured to display any of the number of medical instruments. A microphone may be provided for transmitting voice commands identifying different ones of the number of medical instruments. A controller may be responsive to the voice commands to control the display device to display corresponding ones of the number of medical instruments.

The system may further include means for identifying any of the number of medical instruments. The controller may be responsive to the voice commands to control the means for identifying any of the medical instruments to identify corresponding ones of the number of medical instruments.

The display device may be a heads up display device.

The controller may be configured to be trained to recognize and be responsive to the voice commands identifying any of the number of medical instruments.

The controller may be configured to track a sequence of use and/or duration of use, of ones of the number of medical instruments used in the surgical procedure. The controller may be configured to save the sequence and/or use duration in a database.

At least two of the number of medical instruments may cooperate to form a single instrument. The controller may be configured to control the display device to simultaneously display the at least two of the number of medical instruments to thereby display the single instrument.

The system may be operated in tandem with a computer assisted surgery system.

These and other features of the present invention will become more apparent from the following description of the illustrative embodiments.

DESCRIPTION OF THE ILLUSTRATIVE EMBODIMENTS

For the purposes of promoting an understanding of the principles of the invention, reference will now be made to a number of illustrative embodiments shown in the attached drawings and specific language will be used to describe the same.

Figure 1:
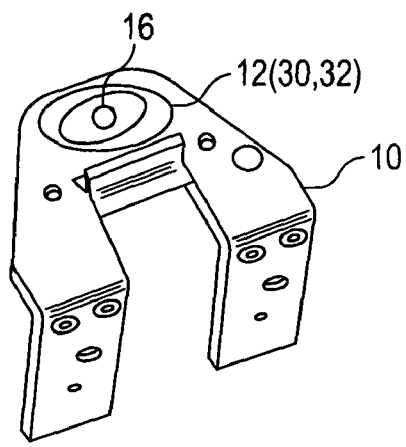
FIG. 1 is a perspective view of a medical instrument having a wireless communication circuit module, including instrument identification electronics, mounted thereto.

Referring now to FIG. 1, a perspective view of a medical instrument 10 is shown having a wireless communication module 12 mounted thereto. The wireless communications module 12 includes a wireless transceiver circuit 30, a battery 32, and an electronic instrument identification component 16, each of which will be described more fully hereinafter. In the illustrated embodiment, the module 12 is provided in the form of a carrier mechanism that may be fabricated of a polymer or other suitable material that will allow the module 12 to be attached to, and removed from, a medical instrument, such as the medical instrument 10, multiple times via a suitable attachment medium or media. The carrier mechanism 12 houses the wireless transceiver circuit 30, battery 32, the instrument identification component 16 and a manually activated switch. In the illustrated embodiment, the instrument identification component 16 incorporates the manually activated switch in the form of a pushbutton LED, although it is contemplated that the manually activated switch may be provided separately from the instrument identification component 16.

The wireless transceiver circuit 30 is configured to communicate with a network operable to manage instrument use during surgical procedure, as will be described in greater detail hereinafter with respect to FIG. 4. In operation, such a network is operable to communicate with the wireless transceiver circuit 30 carried by the module 12, and activate the instrument identification component 16 when the medical instrument 10 is to be used during a particular surgical procedure. The user then presses the pushbutton LED 16, and the wireless transceiver circuit 30 is responsive to the signal produced by pressing the pushbutton LED 16 to broadcast a signal indicating that the medical device 10 is in use. When the user has completed the particular procedure requiring use of the medical device 10, the user again presses the pushbutton LED and the wireless transceiver circuit 30 is responsive to the signal produced by pressing the pushbutton LED 16 to broadcast a signal indicating that use of the medical instrument 10 has been completed. In this manner, the network may thus manage the sequence of medical instruments to be used in a particular surgical procedure by communicating will all medical instruments in the network space and sequentially identifying, and thereby controlling the order of use of, appropriate ones of a number of medical instruments.

Figure 2:
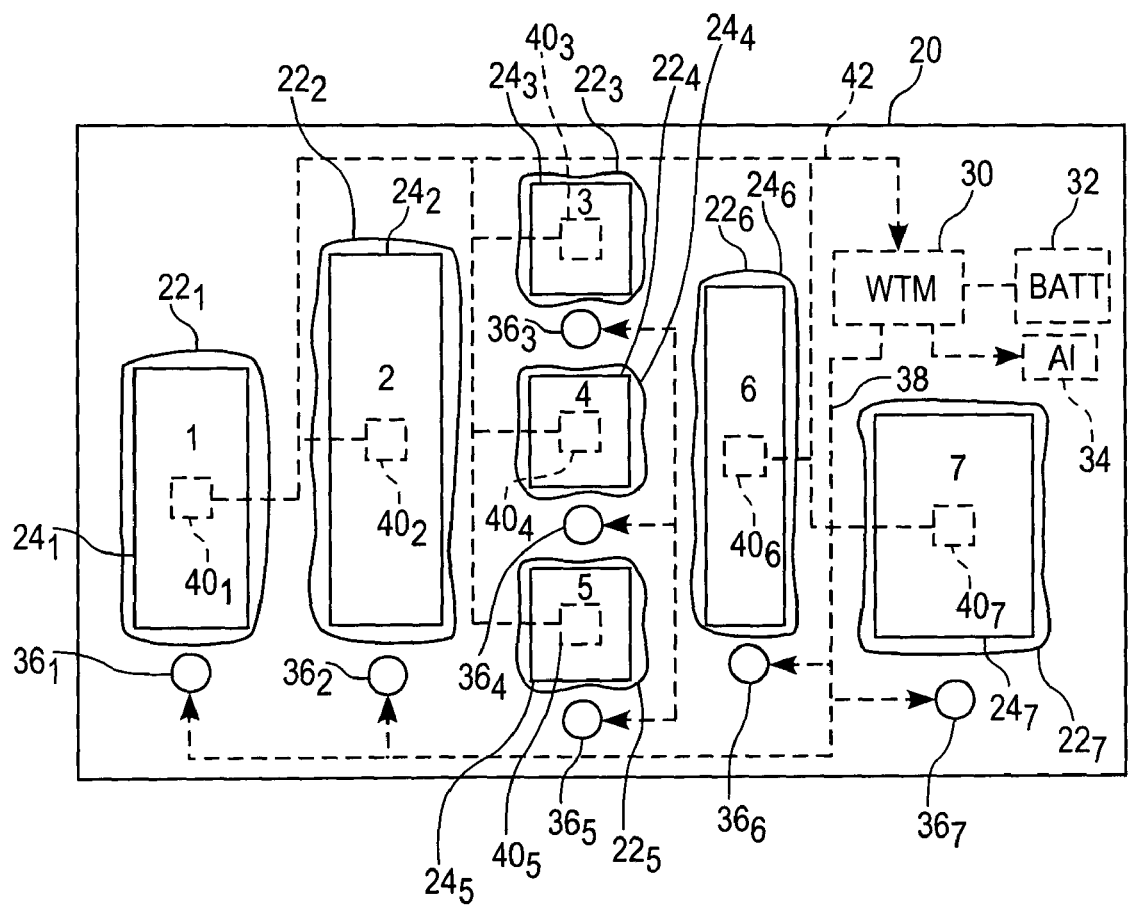
FIG. 2 is a top plan view of one embodiment of a medical instrument tray including instrument identification electronics coupled to a wireless communication circuit.

Referring now to FIG. 2, a top plan view of one embodiment of a medical instrument tray 20, including instrument identification electronic components $36_1$-$36_7$ coupled to a wireless transceiver circuit 30, is shown. The medical instrument tray 20 defines a number of medical instrument storage receptacles $22_1$-$22_7$, each sized and shaped to store a corresponding medical instrument $24_1$-$24_7$ therein. The tray 20 includes a wireless transceiver circuit 30 and a battery 32 mounted thereto, wherein the battery 32 supplies an operating voltage to the wireless transceiver circuit 30. The battery 32 may be a conventional rechargeable or non-rechargeable battery. The wireless transceiver circuit 30 may further have an audible indicator 34 electrically connected thereto, as shown in FIG. 2. The audible indicator 34 may be any conventional electronically actuatable audible device responsive to an electrical activation signal to emit a natural or synthesized audible sound. Examples of conventional devices that may be used as the audible indicator 34 include, but are not limited to, a bell, a buzzer, a chime, or any other audible device configured to produce a single one, series or sequence of sounds in response to the activation signal.

The instrument identification electronic components $36_1$-$36_7$ are, in the illustrated embodiment, provided in the form of individual LEDs each positioned adjacent to a different one of the medical instrument storage receptacles $22_1$-$22_7$. The LEDs $36_1$-$36_7$ are each electrically connected to the wireless transceiver circuit 30 via a multi-wire signal path 38 as illustrated in FIG. 2. The wireless transceiver circuit 30 is configured to activate and deactivate each of the LEDs $36_1$-$36_7$ in a known manner. In one embodiment, each of the LEDs $36_1$-$36_7$ incorporate a manually activated switch in the form of a pushbutton LED as described hereinabove with respect to FIG. 1. Alternatively or additionally, the instrument identification electronic components $36_1$-$36_7$ may be provided in the form of diffuse light sources each embedded within or positioned under a different one of the medical instrument storage receptacles $22_1$-$22_7$. Alternatively or additionally still, the wireless transceiver circuit 30 may be electrically connected to a number of instrument presence sensors $40_1$-$40_7$ via a multi-wire signal path 42, with each sensor positioned within a different one of the medical instrument storage receptacles $22_1$-$22_7$. Each of the number of instrument presence sensors $40_1$-$40_7$ is configured to produce a signal indicative of the presence or absence of a corresponding one of the instruments $24_1$-$24_7$ within a corresponding one of the medical instrument storage receptacles $22_1$-$22_7$. In one embodiment, the sensors $40_1$-$40_7$ are each conventional proximity sensors, although other conventional sensors for detecting the presence and/or absence of an item may be used.

The wireless transceiver circuit 30, in the embodiment illustrated in FIG. 2, is configured to communicate with a network operable to manage instrument use during surgical procedure, as will be described in greater detail hereinafter with respect to FIG. 4. In operation, such a network is operable to communicate with the wireless transceiver circuit 30 carried by the medical instrument tray 20, and instruct the wireless transceiver circuit 30 to activate one of the LEDs $36_1$-$36_7$ when a corresponding one of the medical instruments $24_1$-$24_7$ is to be used during a particular surgical procedure. In embodiments in which the LEDs $36_1$-$36_7$ are pushbutton LEDs, the user then presses a corresponding one of the pushbutton LEDs $36_1$-$36_7$, and the wireless transceiver circuit 30 is responsive to the signal produced by pressing the corresponding one of the pushbutton LEDs $36_1$-$36_7$ to broadcast a signal indicating that the corresponding one of the medical instruments $24_1$-$24_7$ is in use. When the user has completed the particular procedure requiring use of the corresponding one of the medical instruments $24_1$-$24_7$, the user again presses the corresponding one of the pushbutton LEDs $36_1$-$36_7$ and the wireless transceiver circuit 30 is responsive to the signal produced by pressing the corresponding one of the pushbutton LEDs $36_1$-$36_7$ to broadcast a signal indicating that use of the corresponding one of the medical instruments $24_1$-$24_7$ has been completed.

In embodiments in which the medical instrument storage tray 20 includes the instrument presence sensors $40_1$-$40_7$, the network is operable to communicate with the wireless transceiver circuit 30 carried by the medical instrument tray 20, and instruct the wireless transceiver circuit 30 to activate one of the LEDs $36_1$-$36_7$ when a corresponding one of the medical instruments $24_1$-$24_7$ is to be used during a particular surgical procedure. When the user then removes the corresponding one of the medical instruments $24_1$-$24_7$ from its corresponding storage receptacle $22_1$-$22_7$, the corresponding one of the instrument presence sensors $40_1$-$40_7$ produces a signal indicating that the medical instrument has been removed from its storage receptacle. The wireless transceiver circuit 30 is responsive to the signal produced by the corresponding one of the instrument presence sensors $40_1$-$40_7$ to broadcast a signal indicating that the corresponding one of the medical instruments $24_1$-$24_7$ is in use. When the user has completed the particular procedure requiring use of the corresponding one of the medical instruments $24_1$-$24_7$, and the user then places the corresponding one of the medical instruments $24_1$-$24_7$ back into its corresponding storage receptacle $22_1$-$22_7$, the corresponding one of the instrument presence sensors $40_1$-$40_7$ produces a signal indicating that the medical instrument has been placed back into its storage receptacle. The wireless transceiver circuit 30 is then responsive to the signal produced by the corresponding one of the instrument presence sensors $40_1$-$40_7$ to broadcast a signal indicating that use of the corresponding one of the medical instruments $24_1$-$24_7$ has been completed.

In either case, the network may thus proceed in the foregoing manner to manage the sequence of medical instruments to be used in a particular surgical procedure by communicating with all medical instruments in the network space and sequentially identifying, and thereby controlling the order of use of, appropriate ones of a number of medical instruments.

Figure 3:
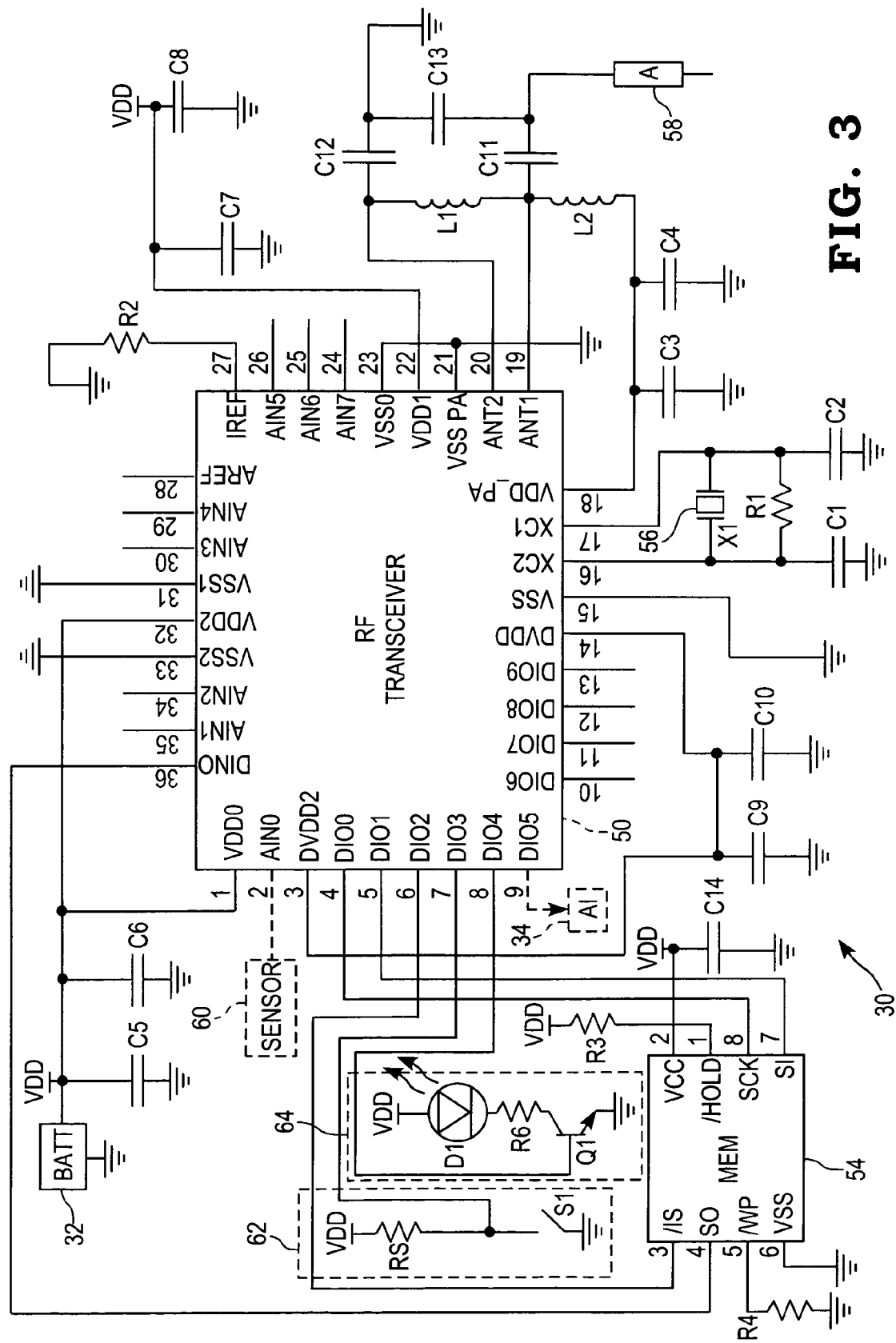
FIG. 3 is a schematic diagram of one illustrative embodiment of a wireless communication circuit carried by the circuit module of FIG. 1 and/or the medical instrument tray of FIG. 2.

Referring now to FIG. 3, a schematic diagram of one illustrative embodiment of the wireless transceiver circuit 30 of FIGS. 1 and 2 is shown. Central to the wireless transceiver circuit 30 is a transceiver circuit 50 operable to broadcast information using conventional wireless communications technology. The transceiver circuit 50 may be, for example, an nRF241E1, 2.4 GHz RF transceiver/transmitter that is commercially available through Nordic Semi-Conductor ASA of Tiller, Norway, although the present disclosure contemplates that the transceiver circuit 50 may alternatively be any known transceiver circuit capable of broadcasting information in the radio frequency range (e.g., 402-405 MHz or so-called MICS band) or other frequency range including, but not limited to, sub radio frequencies, or other conventional protocols including, but not limited to, Bluetooth©, ZigBee©, Wi-Fi, Wireless USB, and the like. The transceiver circuit 50 operates at a supply voltage, VDD, produced by the conventional rechargeable or non-rechargeable battery 32, and at a clock frequency generated by a conventional crystal 56. The crystal 56 in the illustrated embodiment is a 16 MHz crystal, although crystals operating at other clock frequencies may be used.

In the embodiment illustrated in FIG. 3 wherein the transceiver circuit 50 is a nRF241E1, 2.4 GHz RF transceiver/transmitter produced by Nordic Semi-Conductor, such a transceiver circuit does not include sufficient memory for storage of program code and/or any generated data. Accordingly, a separate memory circuit 54 is provided for the purpose of storing one or more executable algorithms and/or storing data. In the illustrative embodiment, the memory circuit 54 is a 4.0 Kbyte serial EEPROM that is commercially available through any number of semiconductor manufacturers. In other embodiments, the transceiver circuit 50 may include sufficient on-board memory, in which case the memory circuit 54 may be omitted.

In the illustrated embodiment, the transceiver circuit 50 is configured for short-range wireless communication within the space of a conventional operating room, and in this regard a single-ended antenna 58 is connected via a differential-to-single ended matching network, comprising L1, L2, C3-C4 and C11-C13 to differential antenna inputs, ANT1 and ANT2, of the transceiver circuit 50. In the illustrated embodiment, the antenna 58 is a 50 OHM antenna that may be implemented in any variety of known antenna configurations.

The wireless transceiver circuit 30 further includes at least one instrument identification electronic component, and in the embodiment illustrated in FIG. 3 one such component is shown in the form of an LED including supporting LED control circuitry 64. In this embodiment, the LED is connected between the supply voltage, VDD, and a control transistor, Q1. The transceiver circuit 50 is operable to control the state of the LED via conventional control of the transistor Q1. In some embodiments, the wireless transceiver circuit 30 further includes at least one switch, and in the embodiment illustrated in FIG. 3 one such switch, S1, is shown with supporting switch control circuitry 62. In this embodiment, one terminal a single pole, single throw switch, S1, is connected to ground potential and the other terminal is connected through a resistor, RS, to the supply voltage, VDD. The transceiver circuit 50 is responsive to the state of the switch, S1, to broadcast certain information as described hereinabove. In embodiments of the wireless transceiver circuit 30 that are mountable to a medical instrument 10 as illustrated in FIG. 1, the wireless transceiver circuit 30 includes one such LED circuit 64 and one such switch circuit 62, wherein the LED circuit and the switch circuit 62 may be combined into a single, pushbutton LED circuit as described hereinabove. Alternatively, the switch circuit 62 and the LED circuit 64 may be provided separately as illustrated in FIG. 3. In embodiments of the wireless transceiver circuit 30 that are mountable to a medical instrument storage tray 20 as illustrated in FIG. 2, the wireless transceiver circuit 30 includes a number of such LED circuits 64. In such embodiments, the wireless transceiver circuit 30 may further include a corresponding number of switch circuits 62, wherein the number of LED circuits 64 and switch circuits 62 may or may not be combined into a pushbutton LED circuits as described hereinabove. Alternatively, the switch circuits 62 may be omitted, and the wireless transceiver circuit 30 may instead include a number of instrument presence sensors as described hereinabove with respect to FIG. 2, although only one such instrument presence sensor 40 is shown in FIG. 3.

The wireless transceiver circuit 30 may further include an audible indicator 34 of the type described hereinabove. In the illustrated embodiment, for example, an audible indicator 34 may be electrically connected to a digital or analog output of the transceiver circuit 50. The transceiver circuit 50 is operable to control operation of the audible indicator 34 in a conventional manner.

The remaining electrical components illustrated in FIG. 3 are provided to support operation of the transceiver circuit 50 and memory circuit 54. Typical values of the illustrated components for one specific implementation of the wireless transceiver circuit 30 are provided in the following Table 1. It will be understood that such component values are provided only way of example, and that other component values may be used.

TABLE 1

| Component Identification | Description | Physical Size | Value | Tolerance | Units |
|---|---|---|---|---|---|
| C1 | Ceramic Capacitor, 50 V, NPO | 0603/0402 | 22 | ±5% | pF |
| C2 | Ceramic Capacitor, 50 V, NPO | 0603/0402 | 22 | ±5% | pF |
| C3 | Ceramic Capacitor, 50 V, NPO | 0603/0402 | 22 | ±5% | pF |
| C4 | Ceramic Capacitor, 50 V, X7R | 0603/0402 | 2.2 | ±10% | nF |
| C5 | Ceramic Capacitor, 50 V, X7R | 0603/0402 | 1.0 | ±10% | nF |
| C6 | Ceramic Capacitor, 50 V, X7R | 0603/0402 | 10 | ±10% | nF |
| C7 | Ceramic Capacitor, 50 V, X7R | 0603/0402 | 10 | ±10% | nF |
| C8 | Ceramic Capacitor, 50 V, X7R | 0603/0402 | 1.0 | ±10% | nF |
| C9 | Ceramic Capacitor, 50 V, X7R | 0603/0402 | 1.0 | ±10% | nF |
| C10 | Ceramic Capacitor, 50 V, X7R | 0603/0402 | 33 | ±10% | nF |
| C11 | Ceramic Capacitor, 50 V, NPO | 0603/0402 | 1.0 | ±0.25 pF | pF |
| C12 | Ceramic Capacitor, 50 V, NPO | 0603/0402 | 1.0 | ±0.25 pF | pF |
| C13 | Ceramic Capacitor, 50 V, NPO | 0603/0402 | 1.5 | ±0.25 pF | pF |
| C14 | Ceramic Capacitor, 50 V, X7R | 0603/0402 | 10 | ±10% | nF |
| L1 | Inductor, wire wound | 0603/0402 | 3.6 | ±5% | nH |
| L2 | Inductor, wire wound | 0603/0402 | 22 | ±5% | nH |
| R1 | Resistor | 0603/0402 | 1.0 | ±1% | Mohm |
| R2 | Resistor | 0603/0402 | 22 | ±1% | Kohm |
| R3 | Resistor | 0603/0402 | 10 | ±1% | Kohm |
| R4 | Resistor | 0603/0402 | 10 | ±1% | Kohm |
| 50 | nRF241E1 (Nordic VLSI) | QFN36/6 × 6 | | | |
| 54 | 4 Kbyte serial EEPROM with SPI interface | SO8 | 2XX320 | | |
| 56 | Crystal, $C_L$ = 12 pF, ESR < 100 ohm | L × W × H = 4.0 × 2.5 × 0.8 | 16 | +/−30 ppm | MHz |

Figure 4:
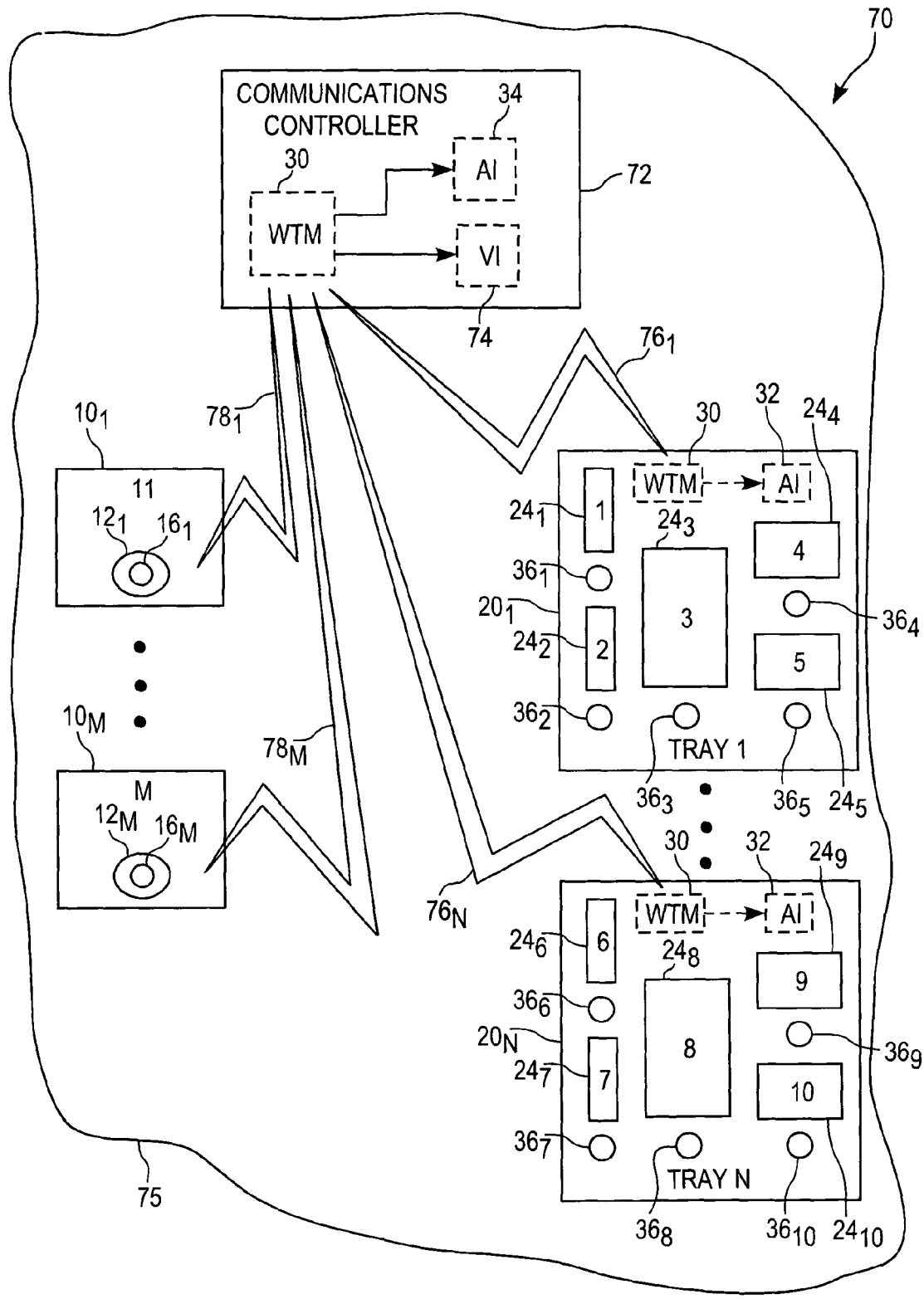
FIG. 4 is a diagram of one illustrative embodiment of an operating room wireless network for identifying appropriate sequences of medical instruments to be used in surgical procedures.

Referring now to FIG. 4, a diagrammatic illustration of one illustrative embodiment of a wireless network environment 70 is shown in the context of a portion of an operating room or other space for performing surgical procedures. In the illustrated embodiment, the wireless network environment 70 includes a communications controller 72, any number, N, of surgical instrument trays 20$_1$-20$_N$ of the type illustrated in FIG. 2, and any number, M, of medical instruments 10$_1$-10$_M$ of the type illustrated in FIG. 1, wherein M and N may each be any positive integer. The communications controller 72 includes a wireless transceiver circuit 30 including either one, or both of, an audible indicator 34 and a visual indicator 74. As described hereinabove, the audible indicator 34 may be any conventional electronically actuatable audible device responsive to an electrical activation signal to emit a natural or synthesized audible sound. Examples of conventional devices that may be used as the audible indicator 34 include, but are not limited to, a bell, a buzzer, a chime, or any other audible device configured to produce a single one, series or sequence of sounds in response to the activation signal. The visual indicator 74 may likewise be any conventional device responsive to an electrical activation signal to emit, produce or display a visible event. Examples of conventional devices that may be used as the visual indicator 74 include, but are not limited to, one or more lamps, light emitting diodes (LEDs), vacuum fluorescent, liquid crystal or other types of displays, monitors or the like.

The wireless transceiver circuits 30 carried by each of the number, N, of medical instrument trays $20_1$-$20_N$ are configured to share information with the wireless transceiver circuit 30 of the communications controller 72 via corresponding wireless communication paths $76_1$-$76_N$. Likewise, the wireless transceiver circuits $12_1$-$12_M$ of the medical instruments $10_1$-$10_M$ are configured to share information with the wireless transceiver circuit 30 of the communications controller 72 via corresponding wireless communication paths $78_1$-$78_M$. In the embodiment illustrated in FIG. 4, the communications controller 72 operates as a "master" or "hub" device and is accordingly operable in a conventional manner to receive all communications from any one or more of the medical instrument trays $20_1$-$20_N$ and any one or more of the medical instruments $10_1$-$10_M$, and to selectively transmit information back to any one or more of the medical instrument trays $20_1$-$20_N$ and/or medical instruments $30_1$-$30_M$. The communications controller 72 continuously performs device discovery by monitoring information broadcast by any one or more of the medical instrument trays $20_1$-$20_N$ and any one or more of the medical instruments $10_1$-$10_M$. In this configuration, each of the medical instrument trays $20_1$-$20_N$ and medical instruments $30_1$-$30_M$ are configured to continually broadcast device identification codes (device ID) unique to the instruments carried by each of the medical instrument trays $20_1$-$20_N$ and unique to the various medical instruments $10_1$-$10_M$. The communications controller 72 is operable to continually determine and monitor the presence of all medical instruments carried by any of the medical instrument trays $20_1$-$20_N$, as well as the various medical instruments $30_1$-$30_M$, that are within the wireless communications network environment 70.

The communications controller 72 is configured to manage the order of medical instruments used in surgical procedures, as described hereinabove with respect to FIGS. 1 and 2, according to predefined surgical procedures executed by the communications controller 72. Information relating to one or more such predefined surgical procedures may be stored in memory, and executed by the communications controller 72 to manage and control medical instrument use during such surgical procedures. Specifically, the communications controller 72 is operable, according to a predefined surgical procedure, to determine whether a first medical instrument to be used during the procedure is present within the network environment 70, as just described. If not, the communications controller 72 may activate the audible indicator 34 and/or visual indicator 74 carried by the communications controller 72. Otherwise, if the communications controller 72 determines that the first medical instrument to be used during the predefined medical procedure is present within the network environment 70, the wireless transceiver circuit 30 broadcasts a message instructing the wireless transceiver circuit 30 associated with the first medical instrument to be used during the predefined procedure to activate the associated instrument identification electronic component, 16 or $36_1$-$36_7$, to thereby provide a visual guide for selecting the first medical instrument. When the first medical instrument is selected and used, a signal is broadcast by the wireless transceiver circuit 30 associated with the first medical instrument indicating that the first medical instrument is in use, as described hereinabove. The wireless transceiver circuit 30 of the communications controller 72 receives this signal and awaits a further signal indicating that the user is finished with the first medical instrument. This further signal is sent by the wireless transceiver circuit 30 associated with the first medical instrument when the user is finished with the first medical instrument, as described hereinabove. When this signal is received by the wireless communication circuit 30 of the communications controller 72, the communications controller 72 then determines whether a second medical instrument to be used in the predefined medical procedure. This process continues until the last medical instrument in the predefined medical procedure is used. It will be understood that the foregoing process may be modified to identify more than one medical instrument; e.g., groups of medical instruments, at a time.

Those skilled in the art will recognize that the wireless communication module 12 illustrated in FIG. 1 may not be attached to all medical instruments due to the small size and insufficient instrument surface area. Such instruments may be stored in medical trays of the type illustrated in FIG. 2, in which case designating such instruments for use during surgical procedures may be accomplished using the techniques described with respect to FIGS. 2 and 4. When it is not possible or practical to store any such medical instruments in a medical tray of the type illustrated in FIG. 2, any such medical instruments will not have any associated medical instrument identification electronics. It is anticipated in such cases that such medical instruments will generally not require identification electronics, and that only the most likely misused other medical instruments will be provided with instrument identifying electronics.

Figure 5:
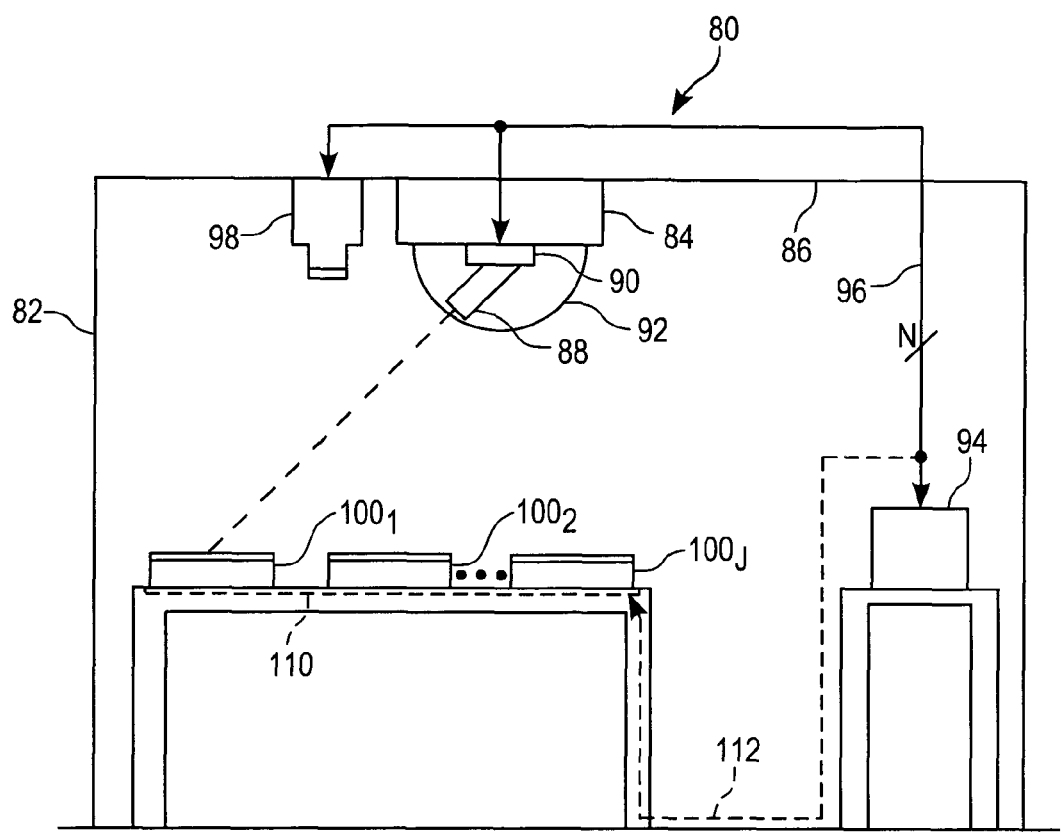
FIG. 5 is a side elevational view of an operating room environment including another illustrative embodiment of a system for identifying appropriate sequences of medical instruments to be used in surgical procedures.

Referring now to FIG. 5, a side elevational view of an operating room environment 82, including another illustrative embodiment of a system 80 for identifying appropriate sequences of medical instruments to be used in surgical procedures, is shown. The present disclosure contemplates that the system 80 may alternatively or additionally be operated in tandem with a computer assisted surgery system. In the illustrated embodiment, the operating room 82 includes a ceiling 86 having an illumination device base 84 mounted thereto. The base 84 includes an illumination device 88 operatively connected to an actuator 90 mounted within the base 84. A light-transmissive cover 92 is mounted to the base 84 to form an enclosure that houses the illumination device 88 and actuator 90. The actuator 90 is electrically connected to a controller 94 via a number, N, of signal paths 96, wherein N may be any positive integer. A conventional video camera 98 may also be mounted to the ceiling 86 or other suitable location, and electrically connected to the controller 94 via one or more of the N signal paths 96. The system 80 further includes a number, J, of medical instrument storage trays positioned on a table or other suitable support, wherein J may be any positive integer.

In one embodiment, the controller 94 is a conventional microprocessor-based computer, e.g., PC, laptop or the like, although the controller 94 may alternatively be any control circuit operable to control and manage medical instrument use during surgical procedures in the manner to be discussed subsequently. The actuator 90 may be a conventional linear, rotating or other actuator configured to orient the illumination device 88 in any desired direction. The illumination device 88 is, in one embodiment, a conventional laser configured to produce radiation in the visible spectrum, e.g., red, although other conventional illumination devices may alternatively be used.

Figure 6:
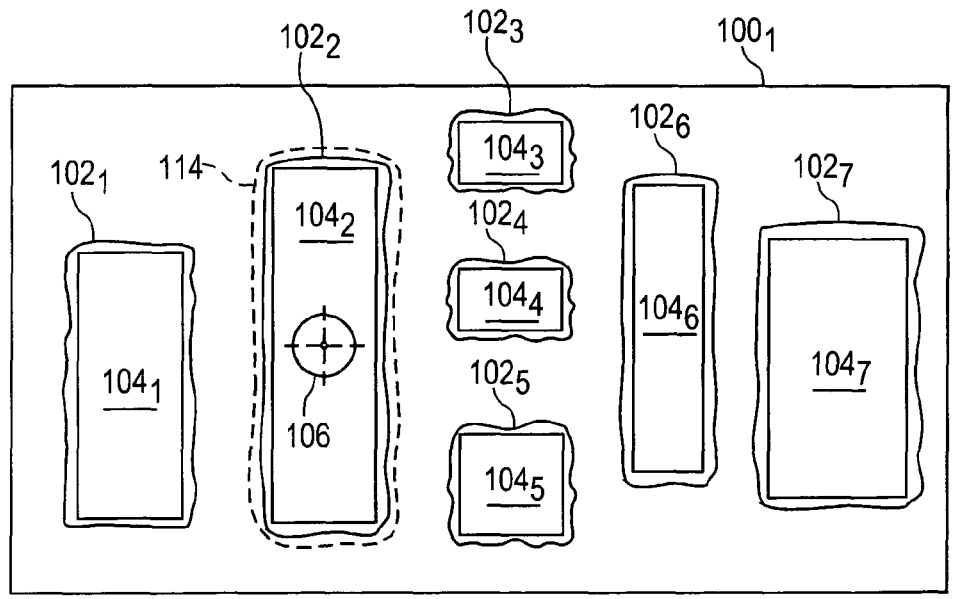
FIG. 6 is a top plan view of one of the medical instrument trays of FIG. 5 illustrating identification of one of the medical instruments for use.

Referring now to FIG. 6, one illustrative embodiment of any of the medical instrument storage trays $100_1$-$100_J$ of FIG.

5, e.g., tray $100_1$, is shown in top plan view. In the illustrated embodiment, the storage tray $100_1$ defines a number, e.g., seven, medical device storage receptacles $102_1$-$102_7$ each having a corresponding one of a number of medical instruments $104_1$-$104_7$ stored therein. As with any medical instrument storage tray embodiment illustrated and described herein, the medical instrument tray $100_1$ may define more or fewer medical device storage receptacles each configured to receive and store a medical instrument therein.

The controller 94 of FIG. 5 includes conventional memory having stored therein one or more software programs defining a sequence of medical instruments to be used for a predefined surgical procedure. In one embodiment, the controller 94 is configured to receive images from the video camera 98, and to process the images to determine the number, type and placement of the various medical trays $100_1$-$100_J$, as well as the contents of each. Based on the images, the controller 94 is then configured to determine coordinates of the various medical instruments contained in the trays $100_1$-$100_J$. Alternatively, each of the trays $100_1$-$100_J$ may be provided with a detectable identifier such as a symbol or other mark. In this embodiment, the controller 94 may be configured to determine from the images only coordinate information relating to the placement of each tray $100_1$-$100_J$ and the tray identifier for each. Medical instrument tray information resident within the controller 94, or loadable into the controller 94, defines coordinates for each instrument in each identified tray relative to a reference position on the trays, e.g., the location of the tray identifier. In another alternative embodiment, the illumination device enclosure 84,92 may include multiple illumination devices, wherein some of the illumination devices are used to project medical instrument storage tray alignment guides onto the medical instrument storage tray support surface to thereby provide for the placement of the medical instrument storage trays $100_1$-$100_J$ at specified locations. In any case, once the location of each tray $100_1$-$100_J$ is determined, the position of each medical instrument within each tray $100_1$-$100_J$ can thus be ascertained from the stored medical instrument tray information. when the one or more software algorithms defining a sequence of medical instruments to be used for a predefine surgical procedure are executed, an initialization procedure is first executed to determine the coordinates, or other location information, of each medical instrument stored in each of the medical instrument storage trays $100_1$-$100_J$.

With the positions of the various medical instruments known, the controller 94 is operable to control the actuator 90 in a conventional manner to direct the light produced by the illumination device 88 to the first medical instrument to be used in the predefined surgical procedure. In the example of FIG. 6, the first medical instrument to be used in the predefined surgical procedure is the medical instrument $104_2$, and the controller 94 is thus operable to control the actuator 90 to direct the light produced by the illumination device 88 to the medical instrument $104_2$. In the illustrated example, the illumination device 88 is a laser configured to produce the light in the form of a pattern 106 positioned on the medical device $104_2$. Those skilled in the art will recognize that other light patterns may be used.

Although not specifically shown in FIG. 5, the system 80 may include any conventional feedback device coupled to the controller 94 for informing the controller 94 when the use of each medical instrument used in the predefined surgical procedure is complete. Examples of such a conventional feedback device include, but are not limited to, a manually activated switch, a keyboard or keypad, a voice-activated command system, and the like. In any case, when the use of each medical instrument identified by the controller 94 as just described is complete, the feedback device is used to inform the controller 94. The controller 94 is then operable to control the actuator 90 to direct the light produced by the illumination device 88 to the next medical instrument to be used according to the predefined surgical procedure. In this manner, the controller 84 is operable to sequentially identify each medical instrument to be used in the predefined medical procedure.

Referring again to FIG. 5, an alternate embodiment of the system 80 may include a light matrix 110 positioned between the medical instrument storage tray support and each of the medical instrument storage trays $100_1$-$100_J$, and electrically connected to the controller 94 via any number of signal paths 112. Alternatively, the light matrix 110 may be embedded into the top surface of the medical instrument storage tray support. In this embodiment, the light matrix 110 may be used in combination with the illumination device 88, or instead of the illumination device 88 in which case the base 84, illumination device 88, actuator 90 and cover 92 may be omitted. In any case, the light matrix 110 includes a matrix of light sources that may be selectively activated to illuminate one or more selected portions of the matrix. As it relates to the system 80 illustrated in FIGS. 5 and 6, the controller 94 is operable, using any one or more of the techniques described hereinabove, to determine the position of each medical instrument in each of the medical instrument storage trays $100_1$-$100_J$ relative to the light matrix 110 prior to the beginning of the predefined surgical procedure. When complete, the controller 94 is operable to control the light matrix 110 to illuminate an area of the light matrix 110 under the first medical instrument to be used in the procedure. If the medical instrument storage trays $100_1$-$100_J$ are at least somewhat light transmissive, this causes the medical instrument tray carrying the first medical instrument to be used in the procedure to become illuminated, as shown by example with the illumination pattern 114 about the medical instrument $104_2$ in FIG. 6. When the controller 94 is informed that use of the first medical instrument to be used in the predefined surgical procedure is complete, using any of the techniques described hereinabove, the controller 94 is then operable to control the light matrix 110 to illuminate an area of the light matrix 110 under the next medical instrument to be used according to the predefined surgical procedure. In this manner, the controller 84 is operable to sequentially identify each medical instrument to be used in the predefined medical procedure.

Figure 7:
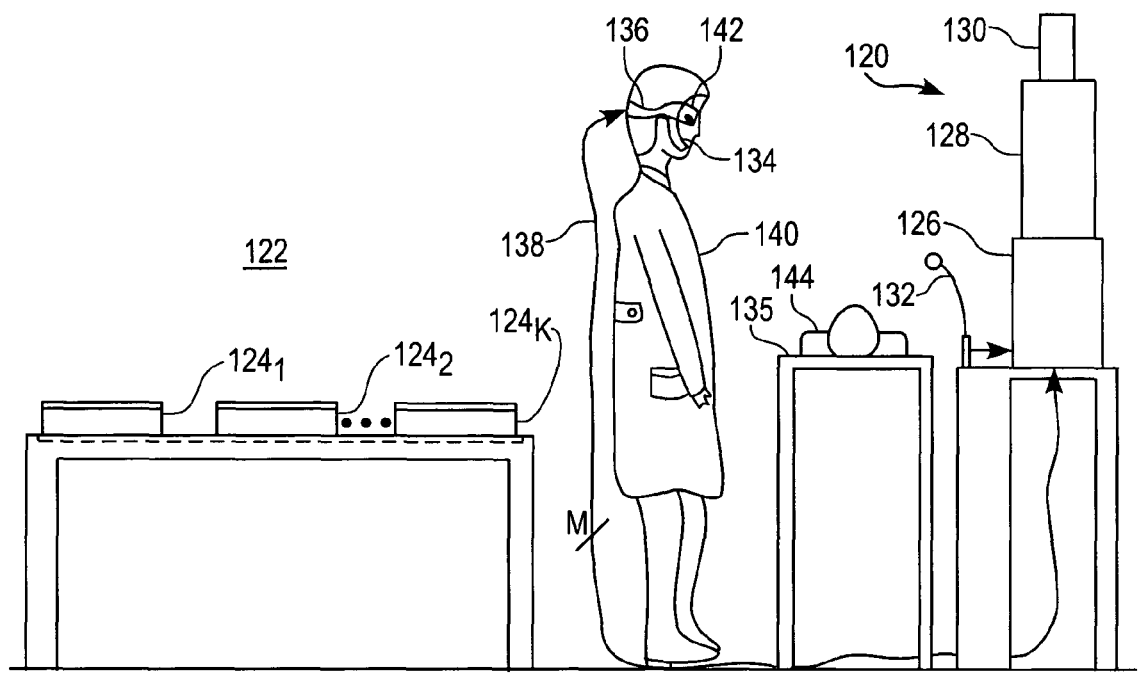
FIG. 7 is a side elevational view of an operating room environment including yet another illustrative embodiment of a system for identifying appropriate sequences of medical instruments to be used in surgical procedures.

Referring now to FIG. 7, a side elevational view of an operating room environment 122, including yet another illustrative embodiment of a system 120 for identifying appropriate sequences of medical instruments to be used in surgical procedures, is shown. The present disclosure contemplates that the system 120 may alternatively or additionally be operated in tandem with a computer assisted surgery system. In the illustrated embodiment, the operating room 122 includes a number, K, of medical instrument storage trays $124_1$-$124_K$, each containing any number of medical instruments, wherein K may be any positive integer. A controller 126 is coupled to a monitor 128, and one or more conventional speakers 130 may be provided to communicate audio information from the controller 126. One or more conventional microphones 132 may also be coupled to the controller 126 for allowing audio information to be provided to the controller 126.

In one embodiment, the controller 126 is a conventional microprocessor-based computer, e.g., PC, laptop or the like, although the controller 126 may alternatively be any control circuit operable to control and manage medical instrument use during surgical procedures in the manner to be discussed subsequently. The monitor 128 is, in one embodiment, a conventional video monitor. Information displayed on the monitor 128 may also be displayed, at least in part, on a conventional heads up display 142 forming part of a head piece 136 worn by a health care professional 140 (e.g., surgeon, scrub nurse, operating room technician, etc.), wherein the head piece 136 is electrically connected to the controller 126 via any number, M, of signal paths 138. The microphone 132 may be supplemented, or replaced by, a conventional microphone 134 that is also carried by the head piece 136. Alternatively or additionally, more than one health care professional may wear a headpiece 136, wherein such a headpiece may include any one or combination of a microphone, heads up display, ear piece or the like. As one specific example, the surgeon may wear a headpiece that includes only a microphone, and a nurse or operating room technician may wear another headpiece that includes only a heads up display.

Figure 8:
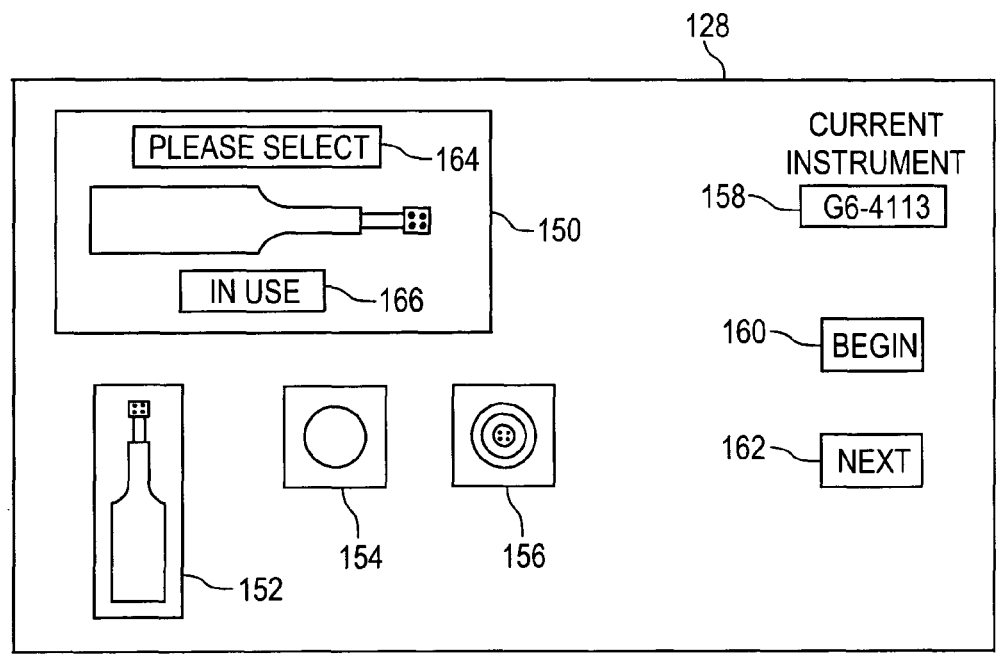
FIG. 8 is an elevational view of the monitor of FIG. 7 illustrating an example medical instrument identification screen.

The controller 126 of FIG. 7 includes conventional memory having stored therein one or more software programs defining a sequence of medical instruments to be used for a predefined surgical procedure. In one embodiment, the memory further has stored therein images and other information relating to each medical instrument to be used in the predefined surgical procedure. In this embodiment, the controller 126 is operable, under control of the one or more software programs defining the sequence of medical instruments to be used for the predefined surgical procedure, to sequentially display the images and other information relating to each medical instrument to be used on the monitor 128 and/or heads up display 142. Referring to FIG. 8, an example window-based screenshot of the monitor 128 is shown of one illustrative layout for displaying medical instrument information and for guiding the user through the sequence of medical instruments specified for the predefined surgical procedure. The monitor 128 has displayed a first window 150 showing one view of a first one of the medical instruments to be used in the predefined surgical procedure. Additional smaller windows 152, 154 and 156 are also provided that show different views of the current medical instrument. Any of the windows 152, 154 and 156 may be selected at any time to exchange the selected instrument view with the view shown in the window 150. The name or other designator of the current instrument, e.g., G6-4113, is displayed in another window 158. Two user selectable icons 160 and 162 also appear on the screen to allow a user to begin the procedure (icon 160) and to display the next instrument to be used (icon 162). The window 150 also includes two messages 164 and 166 that provide feedback to the user. The "PLEASE SELECT" message 164 is highlighted when the user has yet to select for use the medical instrument displayed in the windows 150-156. The "IN USE" message 166 is highlighted when the user has selected for use the medical instrument displayed in the windows 150-156.

In operation, the system 120 is operable to display on the display unit 128 the first medical instrument to be used in the predefined surgical procedure. The user then selects the "BEGIN" icon 160. The user retrieves the displayed medical instrument from the number of storage trays $124_1$-$124_K$, and the "PLEASE SELECT" message 164 is highlighted until the user provides feedback to the system 120, using any one or more of the feedback devices described hereinabove, that the displayed medical instrument is in use. The system 120 is responsive to this information to highlight the "IN USE" message 166. When the user is finished with the displayed instrument, the user selects the "NEXT" icon 162, and the system 120 displays the next medical instrument to be used in the predefined medical procedure on the display unit 128. This process continues until the procedure is complete.

Figure 9:
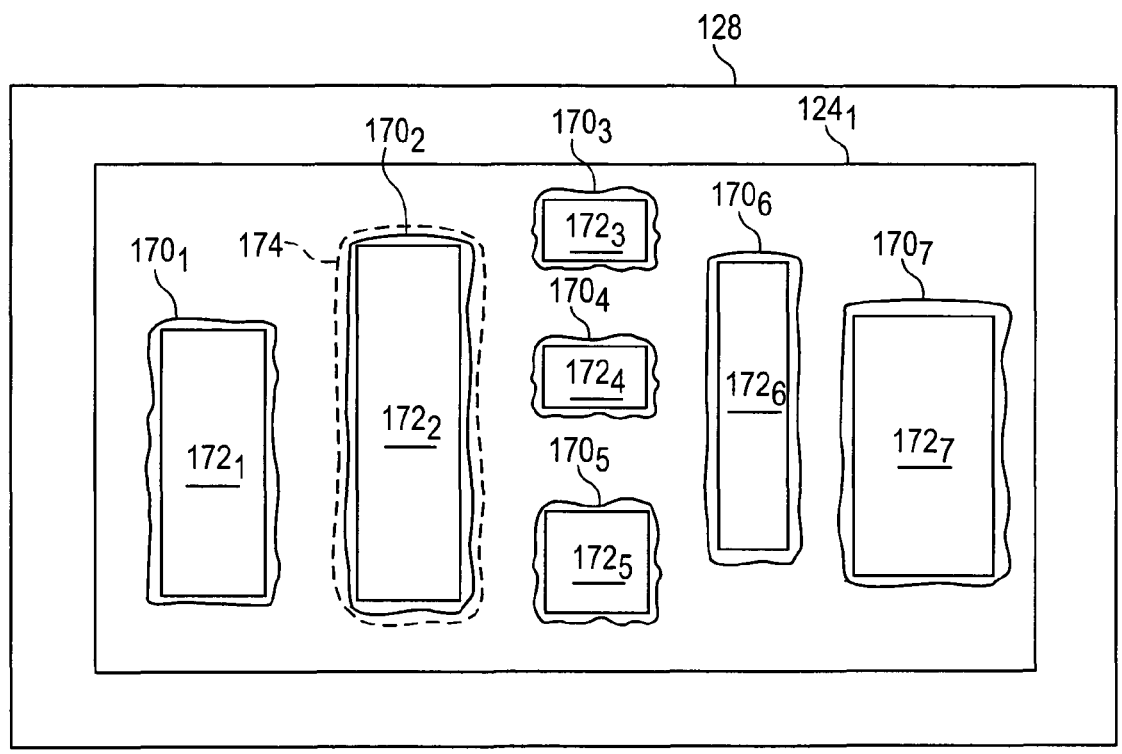
FIG. 9 is an elevational view of the monitor of FIG. 7 illustrating another example medical instrument identification screen.

In an alternate embodiment, the monitor 128 may be configured to display images of appropriate ones of the medical instrument storage tray $124_1$-$124_K$. Referring to FIG. 9, for example, the medical instrument storage tray $124_1$ is shown having a number, e.g., seven, medical instrument storage receptacles $170_1$-$170_7$, each with a corresponding medical instrument $172_1$-$172_7$ stored therein. According to the predefined surgical procedure, the current medical instrument that should be used is the medical instrument $170_2$, which is stored in the medical instrument storage tray $124_1$. The controller 126 thus highlights the medical instrument $172_2$, as illustrated by the dashed line 174, thereby indicating that the medical instrument $172_2$ should be selected for use. For further medical instruments to be used in the predefined medical procedure, the controller 126 is operable to display an appropriate one of the medical instrument storage trays $124_1$-$124_7$, and to highlight for use an appropriate one of the medical instruments carried by the displayed medical instrument storage tray. In another alternate embodiment, the system 120 may include a video projector configured to project an image of the appropriate one of the medical instrument storage trays onto the surgical table 135 on which the patient 144 rests, or other desirable surface. In still another alternate embodiment, the system 120 may include a video camera suitably mounted and operable to capture images of each of the medical instrument storage trays $124_1$-$124_K$ and their contents. In this embodiment, the images of the various medical instrument storage trays $124_1$-$124_K$ projected on the monitor 128, surgical table 135 or other suitable surface are those provided by the video camera. The controller 126, in this embodiment, includes software for matching specific instrument locations with specific medical instrument storage trays.

It will be understood that while a number of different embodiments have been illustrated and described herein for managing and controlling the order or sequence of medical instrument used during surgical procedures, any one or more such embodiments may be combined. For example, the system 80 of FIGS. 5-6 may be combined with the system 120 of FIGS. 7-9. In this example, software resident in the controller allows a user, e.g., the surgeon, to customize the instrument order before beginning the procedure. In this example, the system 120 further includes voice activation/control software that allows the surgeon to train the system 120 to recognize voice commands, e.g., surgical instrument names or other identifiers, surgical process commands such as "begin", "next", "select", "go back", etc., surgical process change commands such as "insert", "delete", "skip", etc. and the like. The present disclosure contemplates that the system 120, as well as any of the other system embodiments described herein, may be configured to allow the surgeon to manipulate the order of surgical instrument use during the surgical procedure. Surgical process change commands represent one technique for allowing the surgeon to effectuate such manipulation in the instrument order for systems that are equipped with voice activation/control software. For example, the surgeon may insert any number of additional instruments into an existing instrument sequence, delete or skip any number of additional instruments from an existing sequence, and/or change the sequence of any number of instruments in an existing instrument sequence. In other embodiments of the systems described herein, such changes may be effectuated manually via one or more switches or the like.

In the current example, the surgeon wears a first headpiece 136 having at least a microphone for issuing voice commands, and a surgical nurse or other operating room technician wears a second headpiece 136 having at least a heads up display for viewing surgical instrument information. Once the instrument usage order is established, two of the illumination devices housed in the enclosure 84, 92 are activated to provide tray alignment marks. Once aligned, the "BEGIN" icon 160 is selected, either by voice command or via manual selection, and the first instrument appears on the screen 128 and/or heads up display worn by the surgical nurse or other operating room technician, on the surgical table and/or other desirable surface and the "PLEASE SELECT" message 164 is displayed. The first instrument resident in one of the medical instrument storage trays is also illuminated or otherwise indicated by the illumination device 88. The surgeon may select this first instrument or select a substitute instrument via voice command or via manual selection. When the first or substitute instrument is selected for use by the surgical nurse or other operating room technician, an "INSTRUMENT SELECTED" icon (not shown) is selected, or feedback is otherwise provided to the controller using any of the feedback techniques described hereinabove, indicating that the first or substitute surgical instrument has been selected for use. When this occurs, the "IN USE" message 166 is displayed. When the user is finished with the instrument, the user selects the "NEXT" icon 162 via voice command or manual selection to proceed to the next step in the predefined surgical procedure. This cycle repeats until the surgical procedure is complete.

In an alternate embodiment of the example just described, the described equipment is provided but no predefined surgical instrument order yet exists in the system controller. According to this variation, the surgeon begins the surgical procedure by calling out via an appropriate voice command a first surgical instrument to be used in the procedure, e.g., "scalpel." The voice activation/control software resident within the system recognizes the voice command and sends an image of the first surgical instrument to the heads up display worn by the surgical nurse or operating room technician. Alternatively or additionally, the system may send the image to a monitor or other display unit. Additionally, although not necessarily, the system may further illuminate, point to or otherwise identify the actual first surgical instrument resident in the operating room using any one or more of the instrument identifying techniques described hereinabove. In any case, the surgical nurse or other operating room technician then selects the first surgical instrument and transfers the instrument to the surgeon. When the surgeon requires another surgical instrument, the surgeon again issues an appropriate voice command for the next desired surgical instrument. Again, the voice activation/control software resident within the system recognizes the voice command and sends an image of the next desired surgical instrument to the heads up display worn by the surgical nurse or other operating room technician. This cycle repeats until the surgical procedure is complete.

With the system just described, it is desirable to include software that allows the system to track the order of instrument use during the surgical procedure, and to upload that information at the surgeon's command (e.g., after a quality control review) to a medical records database resident within, or accessible by, the system. This provides an automatic record of surgical instrument use order and use duration for each surgical procedure, and also provides a surgical instrument use template for future use by the surgeon.

It will be understood that any of the systems described herein may also make use of the voice activation/control and/or heads up display features just described to provide feedback and control to the system and to display information respectively, such as illustrated and described with respect to FIG. 7. The present disclosure further contemplates that the medical instruments and the order in which they are to be used for any surgical procedure may be learned using any of the systems described herein. With voice recognition software and devices, for example, a surgeon may describe the specific medical instruments and their order of use during a surgical procedure. The controller may collect this information and produce an electronic transcript of the procedure that may be provided in hardcopy or electronic form to use as a guide in establishing a predefined surgical procedure for future use. The present disclosure further contemplates that, with any of the systems described herein, the controller may be configured to produce an audible and/or visual warning indication when the wrong instrument has been selected for use. The present disclosure further contemplates that any of the system embodiments illustrated and described herein may be operated in tandem with a computer assisted surgery system. The present disclosure further contemplates that two or more medical instruments or instrument components may be connected together or otherwise cooperate to form a single instrument. Any of the system embodiments illustrated and described hereinabove may thus be configured to simultaneously indicate, point to, display or otherwise identify any two or more such medical instruments to thereby indicate, point to, display or otherwise identify the single instrument during a surgical procedure.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

What is claimed is:

1. A system for managing medical instrument use during a surgical procedure, the system comprising:
   a plurality of medical instrument trays, each of the plurality of medical trays including a plurality of medical instrument storage receptacles,
   a plurality of medical instruments, each medical instrument being positioned in one of the plurality of medical instrument storage receptacles,
   an actuator having a light source coupled thereto,
   a controller to ensure each medical instrument of the plurality of medical instruments is used in an order of use defined by a predefined surgical procedure, the controller ensuring the order of use by sequentially choosing each medical instrument of the plurality of medical instruments in the order defined by the predefined surgical procedure and sequentially generating actuator commands to direct light produced by the light source toward the chosen medical instrument positioned in one of the plurality of medical instrument storage receptacles to guide a user to the chosen medical instrument positioned in the medical instrument storage receptacle of the medical instrument tray, and
   a plurality of feedback devices, each feedback device of the plurality of feedback devices being associated with a medical instrument of the plurality of medical instruments and actuatable to notify the controller when the user has selected the medical instrument associated with the feedback device for use.

2. The system of claim 1 further comprising a display device coupled to the controller, the display device including a display screen configured to display the medical instruments chosen by the controller.

3. The system of claim 2 wherein in response to a notice that the user has selected a medical instrument of the plurality of medical instruments for use, the controller is to cause the display device to display an indication that the user has selected the medical instrument.

4. The system of claim 2 wherein
at least two medical instruments of the plurality of medical instruments cooperate to form a single instrument, and
the controller is to control the display device to simultaneously display the at least two medical instruments of the plurality of medical instruments to thereby display the single instrument.

5. The system of claim 1 wherein each feedback device is actuatable to notify the controller when use of its associated medical instrument is complete.

6. The system of claim 1 wherein in response to a notice that use of a medical instrument of the plurality of medical instruments is complete, the controller is to choose a next medical instrument of the plurality of medical instruments in the order defined by the predefined surgical procedure.

7. The system of claim 1 wherein the system is operated in tandem with a computer assisted surgery system.

8. The system of claim 1 further comprising
a microphone to receive voice commands,
wherein in response to the voice commands, the controller is to choose medical instruments of the plurality of medical instruments per the order specified by a predetermined surgical procedure.

9. The system of claim 8, wherein
in response to the voice commands, the controller generates actuator commands to direct light produced by the light source toward to the chosen medical instrument.

10. The system of claim 8 wherein the controller is configured to be trained to recognize and be responsive to the voice commands identifying medical instruments of the plurality of medical instruments.

11. The system of claim 8 wherein
at least two of the plurality of medical instruments cooperate to form a single instrument, and
the controller is to control a display device to simultaneously display the at least two medical instruments of the plurality of medical instruments to thereby display the single instrument.

12. The system of claim 8 wherein the system is operated in tandem with a computer assisted surgery system.

13. The system of claim 1 wherein the light source includes at least one laser.

14. The system of claim 1 further comprising a heads up display device to display medical instruments chosen by the controller.

15. The system of claim 1 wherein the controller is configured to track a sequence of use of medical instruments of the plurality of medical instruments used in the surgical procedure.

16. The system of claim 15 wherein the controller is configured to save the sequence in a database.

17. The system of claim 15 wherein the controller is configured to track a duration of use of each medical instrument of the plurality of medical instruments used in the surgical procedure.

18. The system of claim 17 wherein the controller is configured to save the duration of use of each medical instrument of the plurality of medical instruments used in the surgical procedure in a database.

19. The system of claim 1, wherein each of the plurality of medical instrument trays comprises
a plurality of feedback devices positioned to associate each feedback device to a medical instrument receptacle and a medical instrument to be stored therein.

20. The system of claim 19, wherein each of the plurality of medical instrument trays further comprises a wireless transmitter to transmit signals of the plurality of feedback devices that notify the controller when the medical instrument associated with the feedback device has been selected for use.

21. The system of claim 19, wherein each feedback device comprises a switch that in response to being actuated generates a signal to notify the controller when the medical instrument associated with the feedback device has been selected for use.

22. The system of claim 21, wherein each feedback device further comprises a light emitting device that lights to identify a medical instrument of the plurality of medical instruments chosen by the controller.

23. The system of claim 19, wherein
a feedback device of the plurality of feedback devices comprises a presence sensor that generates a signal indicative of whether a medical instrument of the plurality of medical instruments is present in a medical instrument storage receptacle associated with the feedback device, and
the controller determines use of the medical instrument based upon the signal generated by the presence sensor.

24. The system of claim 19, further comprising a carrier mechanism mounted to a medical instrument of the plurality of medical instruments, the carrier mechanism comprising a feedback device of the plurality of feedback devices and a wireless transceiver to transmit a notice from the feedback device to the controller.

25. The system of claim 24, wherein the feedback device of the carrier mechanism comprises a light emitting device that lights to indicate the medical instrument has been chosen by the controller for use, and a switch that in response to being actuated generates a signal to notify the controller when the user has selected the medical instrument associated with the feedback device for use.

26. A method of managing medical instrument use during a surgical procedure, the method comprising the steps of:
accessing a predefined surgical procedure to choose a medical instrument of a plurality of medical instruments per an order of use specified by the predefined surgical procedure,
determining a location of the chosen medical instrument positioned in one of a plurality of medical instrument trays,
activating a light source and directing light from the light source toward the chosen medical instrument positioned in the medical instrument tray to provide a visual indication of the chosen medical instrument and guide a user to the medical instrument tray and the chosen medical instrument positioned therein,
receiving a signal from a feedback device associated with the chosen medical instrument that indicates use of the chosen medical instrument is complete,
accessing the predefined surgical procedure in response to receiving the signal from the feedback device associated with the chosen medical instrument to choose a next medical instrument of the plurality of medical instruments to be used per the order specified by the predefined surgical procedure, and repeating the steps of determining, activating, receiving and accessing until completion of the order specified by the predefined surgical procedure.

27. The method of claim 26, further comprising the step of displaying the chosen medical instrument on a video monitor.

28. The method of claim 27 wherein displaying the chosen medical instrument includes displaying at least a subset of the plurality of medical instruments including the chosen medical instrument of the plurality of medical instruments.

29. The method of claim 27 wherein the step displaying the chosen medical instrument includes displaying at least a subset of the plurality of medical instruments including the chosen medical instrument of the plurality of medical instruments.

* * * * *